(12) United States Patent
Matjacic et al.

(10) Patent No.: US 7,086,996 B2
(45) Date of Patent: Aug. 8, 2006

(54) BALANCE RE-TRAINER

(75) Inventors: Zlatko Matjacic, Ljubljana (SI); Thomas Sinkjaer, Gistrup (DK)

(73) Assignee: Medica-Medizintechnik GmbH, Hochdorf (DE)

( * ) Notice: Subject to any disclaimer, the term of this patent is extended or adjusted under 35 U.S.C. 154(b) by 388 days.

(21) Appl. No.: 10/311,106

(22) PCT Filed: Jun. 12, 2001

(86) PCT No.: PCT/DK01/00402

§ 371 (c)(1),
(2), (4) Date: Dec. 13, 2002

(87) PCT Pub. No.: WO01/95980

PCT Pub. Date: Dec. 20, 2001

(65) Prior Publication Data

US 2003/0181299 A1 Sep. 25, 2003

(30) Foreign Application Priority Data

| Jun. 14, 2000 | (DK) | ................................ 2000 00913 |
| Sep. 22, 2000 | (DK) | ................................ 2000 01404 |
| Dec. 14, 2000 | (DK) | ................................ 2000 01876 |
| Mar. 14, 2001 | (DK) | ................................ 2001 00431 |

(51) Int. Cl.
- *A63B 13/04* (2006.01)
- *A63B 3/00* (2006.01)
- *A63B 22/00* (2006.01)

(52) U.S. Cl. ............................ 482/69; 482/121; 482/78

(58) Field of Classification Search .................. 482/69, 482/148, 121–129; D12/130; 472/1; 135/67
See application file for complete search history.

(56) References Cited

U.S. PATENT DOCUMENTS

| 32,109 | A | * | 4/1861 | DeBrame | ............... 280/87.051 |
| 5,275,426 | A | * | 1/1994 | Tankersley | ............. 280/87.051 |
| 5,356,355 | A | * | 10/1994 | Campbell | ..................... 482/43 |
| 5,512,029 | A | * | 4/1996 | Barnard et al. | ............. 482/129 |
| 5,526,893 | A | * | 6/1996 | Higer | ........................ 180/65.1 |
| 5,830,162 | A | * | 11/1998 | Giovannetti | .................. 601/23 |
| 5,947,872 | A | * | 9/1999 | Ryan et al. | .................... 482/51 |
| 6,059,696 | A | * | 5/2000 | Bohmer et al. | ................ 482/54 |
| 6,120,418 | A | * | 9/2000 | Plough | ........................ 482/69 |

OTHER PUBLICATIONS

A Mechanical Apparatus for Arm-Free Therapeutical Paraplegic Standing, Proc. of the International Biomechanics Workshop, Apr. 1999, Enchede, The Nederlands and in Matjačić, Sinkjmr and Johannesen: Unsupported Standing after Spinal Cord Injury, Proc. of the 4th Annual Conference of the International Functional Electrical Stimulation Society, Aug. 1999, Sendai, Japan.
Godall et al: Enhancing postural stability in hemiplegic using externally applied forces, Int. Journal of Rehabilitation, 1985.
Wing, Allison and Jenner. Retraining and retaining balance after stroke, Bailliere's Clinical Neurology, vol. 2, No. 1, Apr. 1993.

* cited by examiner

Primary Examiner—Gregory L. Huson
Assistant Examiner—L. Amerson
(74) Attorney, Agent, or Firm—Herbert Dubno (57) ABSTRACT

A balance training apparatus for supporting an individual with a limited liability to maintain his or her on balance has a pair of vertical support rods connected to a base by joints which include lower elastic parts tending to bias the user into an upright position. The two support rods are connected by a brace for supporting the pelvis of the user and knee supports are provided between the two support rods for yieldably pressing the knees of the user.

16 Claims, 8 Drawing Sheets

BALANCE RE-TRAINER

CROSS REFERENCE TO RELATED APPLICATIONS

This application is a national stage of PCT/DK 01 00 402 filed 12 Jun. 2001 and is based upon Danish applications PA 2000 00913 filed 14 Jun. 2000; PA 2000 01404 filed 22 Sep. 2000; PA 2000 01876 filed 14 Dec. 2000; PA 2001 00431 filed 14 Mar. 2001 under the International Convention.

FIELD OF THE INVENTION

The present invention relates to a balance training apparatus which is suited for supporting individuals with a reduced ability to maintain balance while standing for retraining purposes, comprising means for biasing a user towards an upright position when deviating therefrom in a frontal plane as well as in a sagittal plane of the individual. The invention also relates to an apparatus comprising a variable spring system that combines a 2-degrees-of-freedom joint with the biasing means into a single element in a simple and advantageous construction.

The present invention further relates to a balance training apparatus comprising compliant knee supporting means arranged to support the front side of the upper end of the shanks and following the movements of the individual in the said two planes, so as to assisting the knee extensor muscles for retraining purposes.

BACKGROUND OF THE INVENTION

Standing-balance training is a crucial therapeutic procedure in rehabilitation of neurologically impaired individuals. Modem concepts of neurological rehabilitation favor task-oriented therapy, where one needs to practice balancing in order to re-learn to balance.

Various neuromuscular disorders reduce the ability of an impaired individual to effectively maintain balance while standing. Impaired individuals can be divided into two groups according to their residual balancing abilities. The first group is comprised of subjects with diminished ability (e.g. hemiparesis, paraparesis and tetraparesis), while the second group is characterized by severe impairment (hemiplegia) or complete loss of balancing abilities (paraplegia and tetraplegia).

The goal of neurological rehabilitation for the group of individuals with diminished balancing abilities is to retrain the residual peripheral and central nervous system in order to develop alternative movement strategies needed to co-ordinate motor behavior as efficiently as possible within the constraints posed by the injury. Different methods facilitating the balance re-learning process have been developed. The common techniques include the use of oscillatory platform movements while the impaired individual is standing on the platform, or to provide biofeedback on weight distribution. Both methods aim to improve balancing abilities in impaired individuals. However, these methods should be applied with caution as the subjects are exposed to situations of destabilization. There is an inherent problem of protecting the subject from falling, which must be solved to ensure safety. Unfortunately, safety implementations in turn pose a significant limitation to the outcome of a training process.

Such methods cannot be applied to the group of severely impaired individuals since they are unable to stand without assistance. Consequently, they are often confined to a sitting position, which can result in various medical complications requiring prolonged and expensive professional medical treatment. A common therapy method for the second group is passive standing in rigid standing frames or tilt tables. These therapies are rather static and hence an unattractive activity since they do not require a sufficient degree of cognitive involvement.

A known device, disclosed in Matjačić and Sinkjwr. A Mechanical Apparatus for Arm-Free Therapeutical Paraplegic Standing, Proc. of the International Biomechanics Workshop, April 1999, Enchede, The Nederlands and in Matjačić, Sinkjmr and Johannesen: Unsupported Standing after Spinal Cord Injury, Proc. of the 4th Annual Conference of the International Functional Electrical Stimulation Society, August 1999, Sendai, Japan provides an impaired individual with a fall-safe balancing environment, where the balancing efforts of a standing individual are augmented by stabilising forces acting at the level of the pelvis in the sagittal and frontal planes of motion, assisting the balancing activity of ankle muscles (sagittal plane) and ankle and hip muscles (frontal plane). The biasing means disclosed comprises two hydraulic motors which may be used for actively biasing a user in a given direction or may be used for providing a resilient effect, described as being equivalent to a passive spring effect. However, a system of hydraulic motors is expensive to produce, complex to operate and requires frequent maintenance to function properly. Moreover, such system is rather space consuming and is all in all only suited for experimental purposes in a scientific context and is not suited for use in rehabilitation training in clinics and in particular not suited for use at home of the individuals in need of training.

Another device, more remote from the present invention, is disclosed in Godall et al: Enhancing postural stability in hemiplegic using externally applied forces, Int. Journal of Rehabilitation, 1985 and in Wing, Allison and Jenner. Retraining and retaining balance after stroke, Bailliere's Clinical Neurology, Vol. 2, No. 1, April 1993, in which the individual is supported by a belt at the hip level on which two actuators act in a horizontal plane in perpendicular directions so that the individual may be supported and at the same time purposely be pushed or disturbed for training and evaluation purposes. This device has the same drawbacks as that which is above-discussed and is intended mainly for scientific purposes.

OBJECTS OF THE INVENTION

It is thus an object of the present invention to provide a balance training apparatus which is suited for supporting individuals with a reduced ability to maintain balance while standing for retraining purposes, comprising means for biasing a user towards an upright position when deviating therefrom in a frontal plane as well as in a sagittal plane of the individual in which the biasing means are of simple, inexpensive construction.

SUMMARY OF THE INVENTION

During use of the device, it may be necessary to keep the knees of the user, the standing individual, extended if the individual is not able to do so on its own. This is with the above-discussed prior art obtained by means of stiff plastic braces. An alternative piece of equipment is a transverse, stiff beam connecting the two vertical rods of a similar device and supporting the individuals on the front below the knees so as to keep the knees in full extension as disclosed in Matjačić and Bajd: Arm-Free Paraplegic Standing—Part II: Experimental Results, IEEE Trans. on Rehabilitation Eng., Vol. 6, No. 2, June 1998. The training of the function of the muscles controlling the knees has, with the known devices, to be performed with other means. It has been found that a surprisingly improvement of the balance training can be obtained by supporting the individuals knees in an extended position in a compliant manner by means of supporting means arranged to support the front side of both legs of the individual near an upper end of the shanks, when the knee supporting means is arranged to follow the movements of the user in the frontal plane as well as in the sagittal plane. Thereby, the individual may during the balance training enhance the training of the balance about the vertical postural axis which mainly is controlled by the knee joints.

Feedback systems for providing the individual with information about its inclination from vertical is known, e.g. from the above-mentioned Matjačić and Bajd: Arm-Free Paraplegic Standing—Pad II: Experimental Results, IEEE Trans. on Rehabilitation Eng., Vol. 6, No. 2, June 1998, in which an audio signal is provided indicating the inclination in the sagittal plane and a visual feedback system indicating the inclination in both planes for training purposes is disclosed in Nichols: Balance Retraining After Stroke Using Force Platform Biofeedback, Physical Therapy, Vol. 77, No. 5, May 1997. The training program disclosed in the latter article is intended for use with a force platform on which the individual to be trained is standing but such computer programs may as well be used with the apparatus of the present invention. A preferred computer training system is disclosed below in which a number of improvements are included, in particular the introduction of a "dead zone", a range of inclination around the vertical position in which the cursor on the visual output screen presented to the individual does not move, such that the individual is forced to move to higher inclinations than the dead zone to activate the computer and to use the training apparatus e.g. as a computer pointing device.

The above object of the invention is reached by integrating the joint between the base and the vertical rod and the biasing means for keeping the user from falling. Thus the present invention relates to a balance training apparatus comprising:

two vertical supportive rods, each connected at a lower end to a base by a joint having two degrees of freedom, a bracing means suitable for supporting the pelvis of a user standing between the two vertical supporting rods, the bracing means being connected to an upper end of each of the vertical supportive rods by a joint having one degree of freedom allowing mutual movement between the bracing means and the vertical rods in the plane of the two vertical rods, biasing means for biasing the user towards an upright position when deviating therefrom in a frontal plane as well as in a sagittal plane of the user, wherein at least one of the vertical rods has a lower, elastic part connecting a stiffer, upper part of the rod to the base and constituting the joint there between as well as constituting the biasing means, and the apparatus further comprises:

adjustment means for adjusting the stiffness of the lower, elastic part.

By integrating the joint and biasing means by employing an elastic part of at least one of the vertical rods, the construction is simplified and readily can be made inexpensive and with low maintenance requirements. It is sufficient that one of the rods has the elastic part, but it is for reasons of symmetry of forces preferred that each of the two vertical rods has a lower, elastic part connecting a stiffer, upper part of the rod to the base and constituting the joint there between as well as constituting the biasing means.

The elastic part may be manufactured from e.g. natural or synthetic rubber, from flat springs being arranged with perpendicular axis of resilience on the two rods, etc., but it has been found that it is most suitable that the elastic part is constituted by a vertical, helical spring which is largely maintenance-free, inexpensive and can be found off-the shelf with suitable elastic properties.

It is also preferred that the apparatus further comprises limitators for limiting the angle of inclination from vertical for each of the vertical rods so that the users do not risk to reach too extreme positions and that the whole apparatus will not tip over as a result thereof.

A preferred way of adjusting the stiffness of the lower, elastic part is to employ adjustment means that may adjust the effective length of the lower, elastic parts. This may be achieved e.g. by displacing a rod vertically inside a helical spring constituting the elastic part, but it is preferred that the adjustment means for each vertical rod comprises an outer mantle arranged around the elastic part with an inner, vertical surface of the mantle fitting around the outer side of the elastic part, the mantle being vertically displaceable such that the effective length of the elastic part is adjusted thereby. The limitators may for such arrangement preferably be connected to the mantles so that they are displaced together therewith and define circular openings through which the vertical rods pass.

It is furthermore advantageous that the apparatus comprises locking means for temporarily locking each of the vertical rods in a vertical position for use when users are entering or leaving the apparatus and for locking the rods when the stiffness of the elastic part is adjusted. The locking means may be connected to the above-described mantle and be displaced together therewith.

It is, for the support of users that do not possess the ability to keep the knees extended, an advantage that the apparatus further comprises knee supporting means arranged to support the front side of both legs of the user near an upper end of the shanks, the knee supporting means being arranged to follow the movements of the user in the frontal plane as well as in the sagittal plane. It is furthermore for knee training purposes as discussed above an advantage that the knee support means are compliant. It is yet further an advantage that the compliance of the knee supporting means is adjustable.

It is also preferred that the apparatus comprises sensor means for measuring the inclination of in the frontal plane as well as in the sagittal plane of the vertical rods and producing an output accordingly so that an evaluation and/or a feed back system may be established.

The invention is also a balance training apparatus comprising two vertical supportive rods, each connected at a lower end to a base by a joint having two degrees of freedom, a bracing means suitable for supporting the pelvis of a user standing between the two vertical supporting rods, the bracing means being connected to an upper end of each of the vertical supportive rods by a joint having one degree of freedom allowing mutual movement between the bracing means and the vertical rods in the plane of the vertical rods, biasing means for biasing a user towards an upright position when deviating therefrom in a frontal plane as well as in a sagittal plane of the user, wherein the apparatus further comprises compliant knee supporting means arranged to support the front side of both legs of the user near an upper end of the shins, the knee supporting means being arranged to follow the movements of the user in the frontal plane as well as in the sagittal plane.

BRIEF DESCRIPTION OF THE FIGURES

A preferred embodiment of the present invention is illustrated in the accompanying drawing in which.

DETAILED DESCRIPTION OF EMBODIMENT

The preferred embodiment of the present invention disclosed herein provides an impaired individual with a fall-safe balancing environment, where the balancing efforts of a standing individual are augmented by stabilizing forces acting at the level of pelvis in the sagittal and frontal planes of motion, assisting the balancing activity of ankle muscles (sagittal plane) and ankle and hip muscles (frontal plane) and at the level of shanks, assisting the knee extensor muscles. The level of supporting forces can be varied from zero up to the level where no balancing activity is needed from the standing subject. Additionally, movement in the sagittal and frontal planes, acquired by transducers, is fed to an electronic interface which transforms the current inclinations into computer mouse, joystick or similar pointing device signals which are interfaced to a personal computer (PC). Thus, a standing subject, by voluntarily changing the posture in the sagittal and frontal planes, can control various software applications running on the PC. Further, an advanced balance training and evaluation program is described, which is designed to facilitate and test balancing in the whole range of anterio-posterior and medio-lateral postural space in a gradual and systematic way, thus enabling uniform neuro-rehabilitation program and objective evaluation of (balancing abilities of a standing subject.

Figure 1:
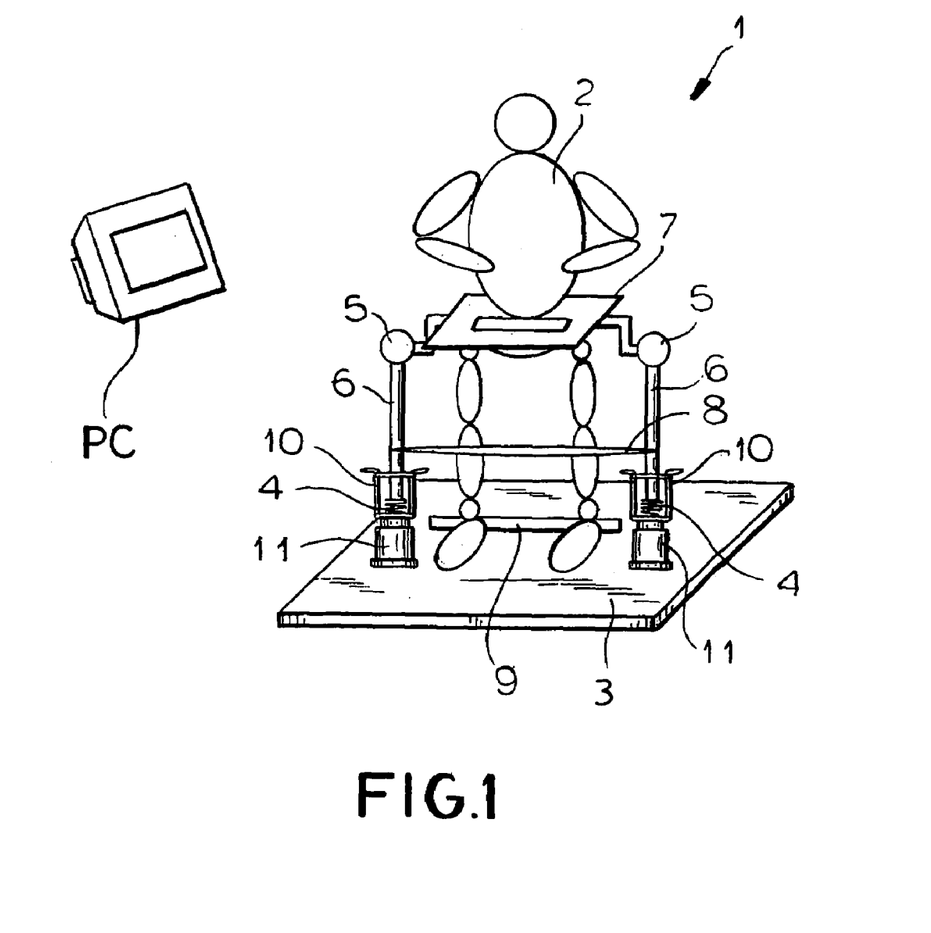
FIG. 1 is a perspective view of the apparatus complete with the base plate and showing an individual situated in the apparatus.
Figure 2:
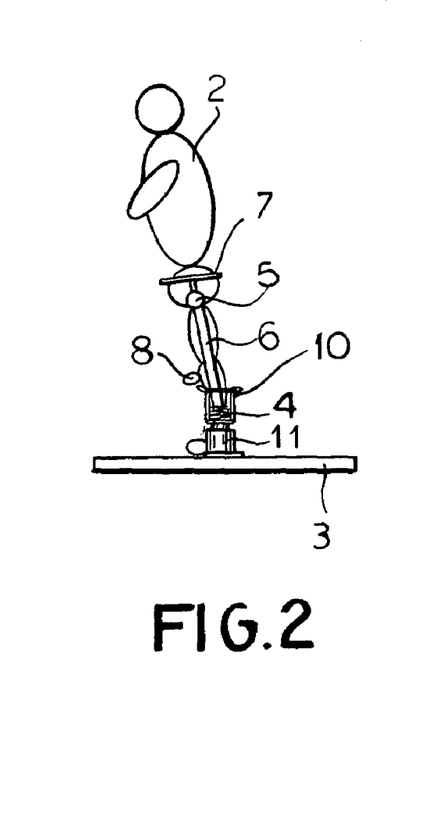
FIG. 2 shows the apparatus of FIG. 1 as seen from the side, in which the individual is inclining forward in the sagittal plane.
Figure 3:
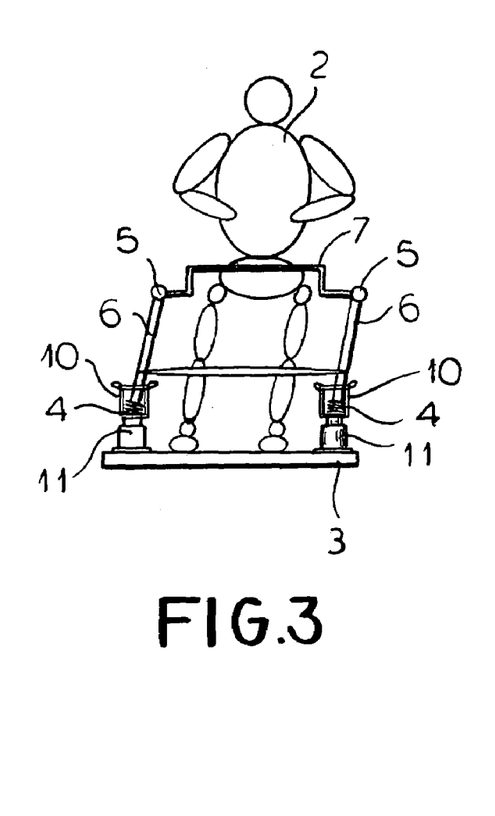
FIG. 3 shows the apparatus of FIG. 1 as seen from the front, in which the individual is inclining in the frontal plane.
Figure 4:
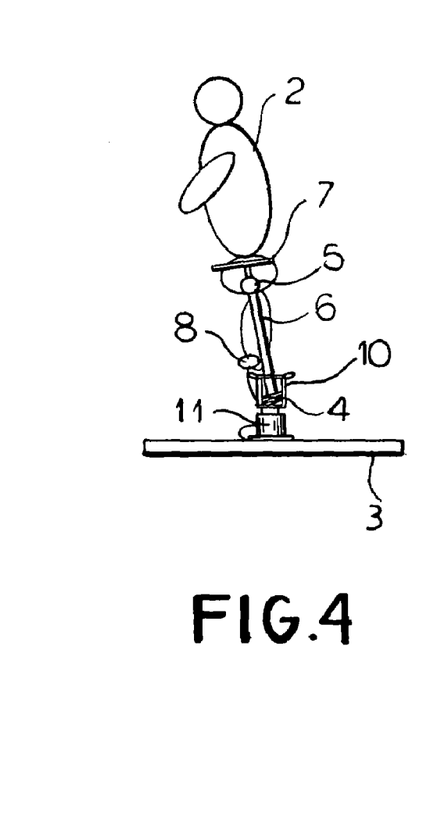
FIG. 4 shows the apparatus of FIG. 1 as seen from the side, in which the individual is inclining forward in the sagittal plane and concurrently is flexing the knees, whereby the knee support comes into action.

FIG. 1 shows a schematic drawing of the apparatus 1 and an individual 2 standing in it. The apparatus consists of the base plate 3, two 2-degrees-of-freedom variable spring systems 4 with an adjustable stiffness of 0 to e.g. 15 Nmldegree, two 1-degree-of-freedom joints 5, two vertical supportive rods 6 of adjustable heights, a size adjustable bracing system 7, a stiffness adjustable compliant band 8, a heel stop 9 and two movement limitators 10. Both 2-degree-of-freedom variable spring systems 4, having adjustable stiffness, are mounted to the base plate 3 and are linked to 1-degree-of-freedom joints 5 by vertical supportive rods 6. A person 2 is standing on the plate 3 with heels placed in front of the heel stop 9, having the pelvis supported by the bracing system 7 and shanks supported by the adjustable compliant band 8. The apparatus 1 has the following three degrees of freedom as shown in FIGS. 2–4:

1. The inclination in the sagittal plane as illustrated in FIG. 2, in which the inclination is mechanically limited to, e.g., ±15 degrees by means of movement limitators.

2. The inclination in the frontal plane as illustrated in FIG. 3, in which the inclination is mechanically limited to, e.g., ±15 degrees by means of movement limitators.

3. The knee flexion as illustrated in FIG. 4, in which the inclination is mechanically limited to, e.g., 15 degrees by means of slack stiff wires incorporated in the adjustable compliant band.

Figure 5:
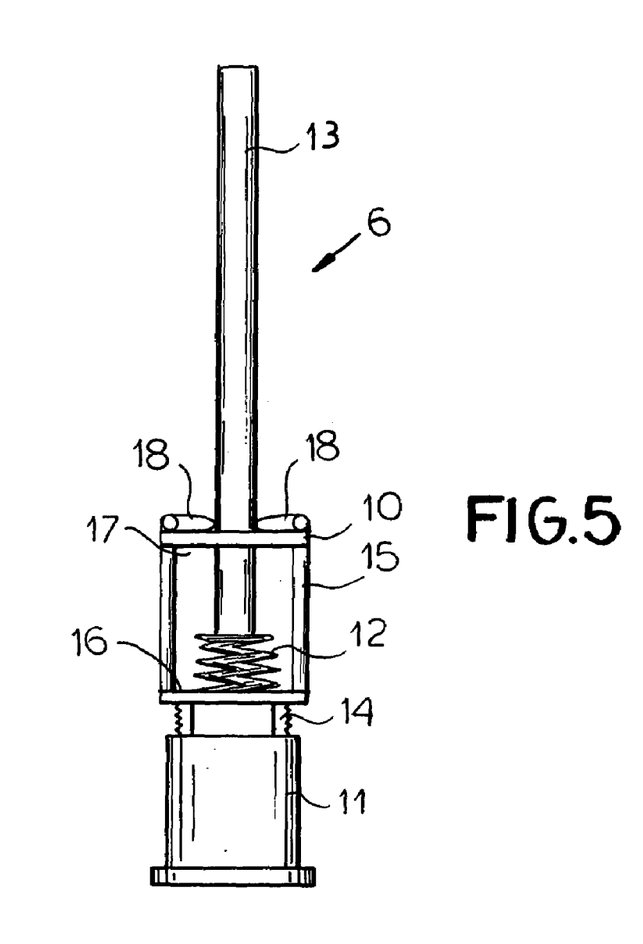
FIG. 5 shows the lower part of a vertical rod as seen from the side with the locking means in a locked position.
Figure 6:
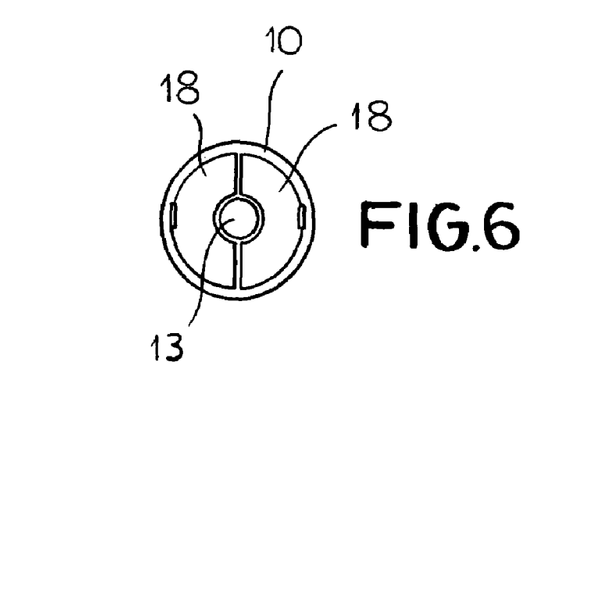
FIG. 6 shows the locking means of FIG. 5 as seen from above.
Figure 7:
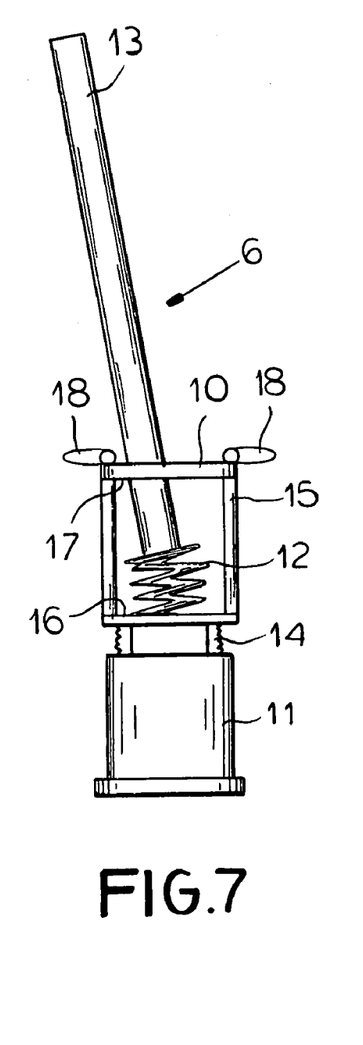
FIG. 7 shows the lower part of a vertical rod as seen from the side with the locking means in an unlocked position and the upper part of the rod in an inclined position.
Figure 8:
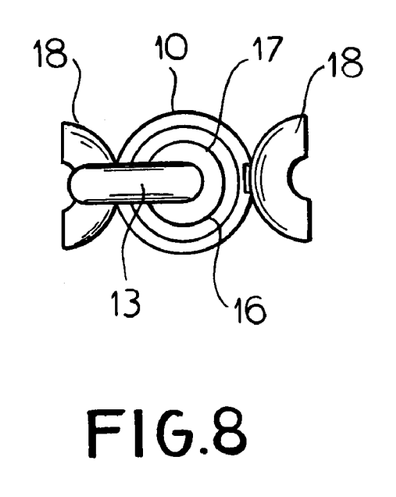
FIG. 8 shows the locking means of FIG. 7 as seen from above.

The variable spring system 4 and the features and functions are shown in detail in FIGS. 5–14. FIG. 5 shows the lower part of a vertical rod with the 2-degrees-of-freedom variable spring system 4 as seen from the side. It consists of a base cylinder 11 connected to the base plate 3, a helical spring 12 connected at the lower end to the base plate 3 and at the upper end to a stiff part 13 of the vertical rod 6, an adjustment cylinder 14 which is an outer mantle around the spring 12 with an inner surface fitting to the outer side of the spring 2. The adjustment cylinder 14 is in threaded engagement with the base cylinder 11 and may be displaced vertically by turning. On top of the adjustment cylinder 14 is a distance piece or space 15 to create a vertical distance between the upper rim 16 of the adjustment cylinder 14, above which rim 16 the spring 12 may bend, and the limitator 10 that has a circular opening 17 through which the stiff part 13 of the vertical rod 6 passes. A pair of lock plates 18 are hinged to the limitator 10 and may be switched between a locked position as shown in FIGS. 5 and 6 in which the two semi-circular openings in the plates 18 lock the rod 6 in a substantially vertical position, and an unlocked position as shown in FIGS. 7 and 8 in which the lock plates 18 are turned away from the rod 6 and allow it to assume an inclined position.

By rotating the adjustment cylinder 14, the free, effective length of the spring 12 may be varied, thus varying also the mechanical stiffness of the 2-degree-of-freedom variable spring system 4. Thus, the variable spring system 4 disclosed herein combines a 2-degree-of-freedom joint and biasing means for biasing a user 2 towards an upright position when deviating therefrom in a frontal plane as well as in a sagittal plane of the user 2 into a single element, which is of low cost, easy to produce and practically maintenance-free and which is highly compact. Other functions, such as the limitators 10 for limiting the inclination of the vertical rods 6 and the locking mechanism 18, are easily integrated in the disclosed variable spring system 4. The locking mechanism consisting of the two, hinged lock plates 18 is used for stabilizing the training apparatus 1 when e.g. an individual 2 enters or leaves the apparatus 1 or when the stiffness of the spring system 4 is adjusted by turning the adjustment cylinder 14.

Figure 9:
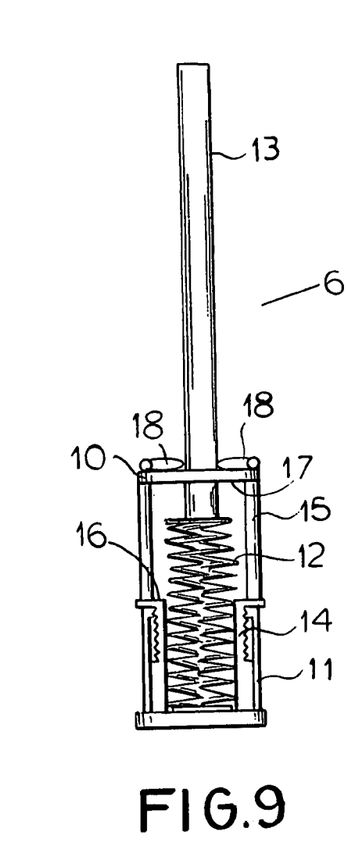
FIG. 9 shows a vertical section of the lower part of a vertical rod as seen from the side with the locking means in a locked position.
Figure 10:
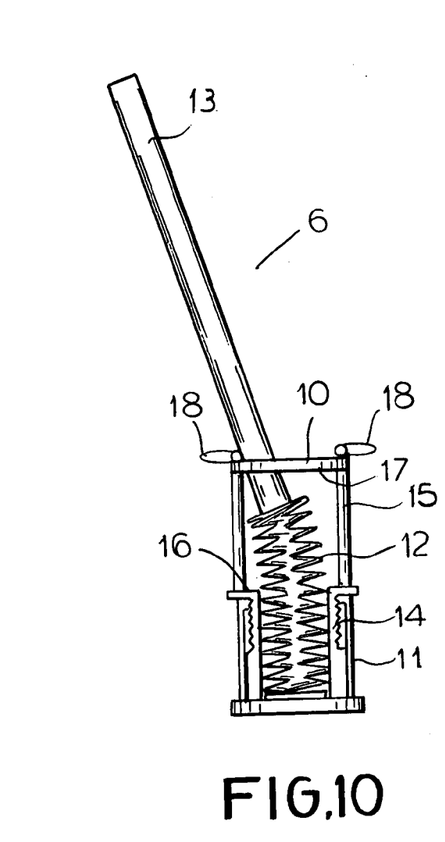
FIG. 10 shows a vertical section of the lower part of a vertical rod as seen from the side with the locking means in an unlocked position and the upper part of the rod in an inclined position.
Figure 11:
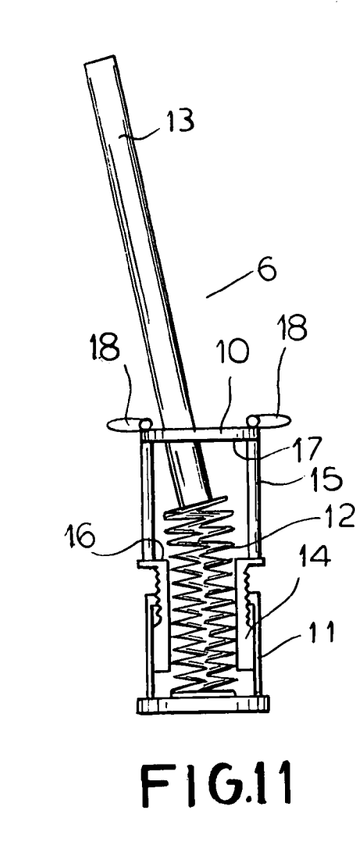
FIG. 11 shows a vertical section as in FIG. 10 wherein the adjustment cylinder is adjusted upwardly to provide a higher stiffness.

Vertical sections of the variable spring system 4 are shown in FIGS. 9–11, in which the bending of the spring 12 and the effect of the vertical displacement of the adjustment cylinder 14 is demonstrated. A vertical section of the! lower part of a vertical rod 6 as seen from the side is shown in FIG. 9 with the locking means 18 in a locked position and in FIG. 10 with the locking means 18 in an unlocked position and the stiff, upper part 13 of the rod 6 in an inclined position. The lower part of the spring 12 is supported on the outer side by the inner side of the adjustment cylinder 14 such that the spring 12 only bends from the vertical level of the upper rim 16 of the adjustment cylinder 14. Thus, the effective length of the spring 12 is reduced, thereby increasing the stiffness of the variable spring system 4 in the position of the adjustment cylinder 14 shown in FIG. 11 as compared to the position shown in FIG. 10 due to the higher vertical position of the upper rim 16.

Figure 12:
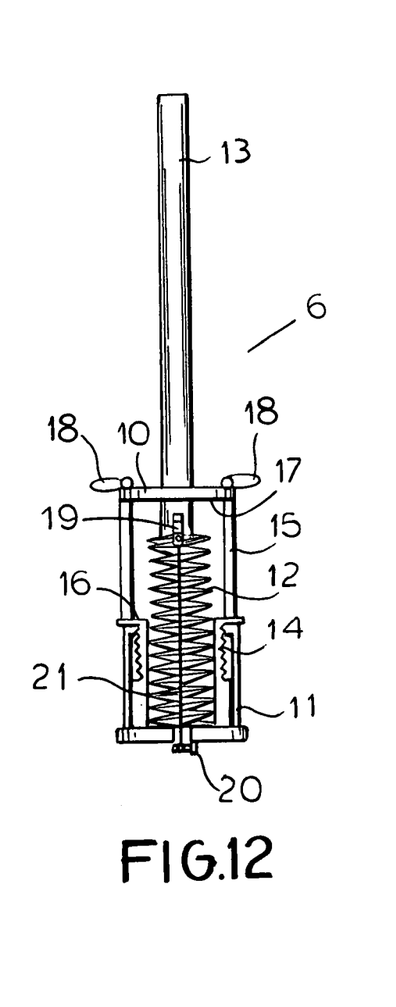
FIG. 12 shows a vertical section in the sagittal plane of the lower part of a vertical rod disclosing the inclination sensor for the frontal plane.
Figure 13:
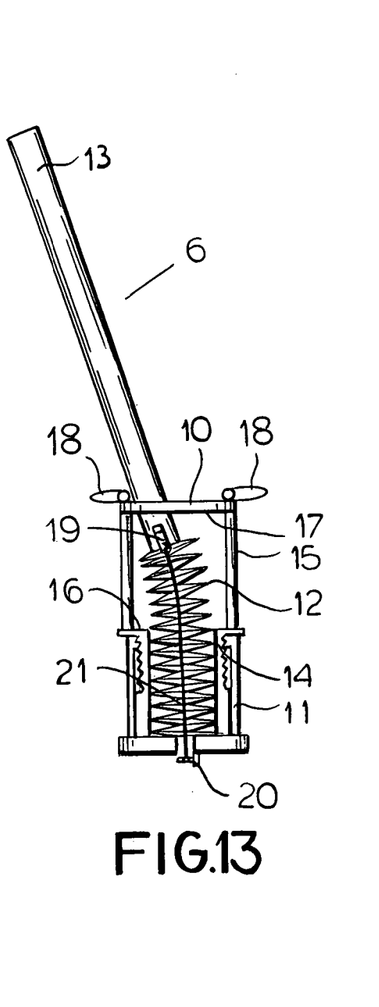
FIG. 13 shows the section of FIG. 12 in which the upper part of the rod is inclined in the sagittal plane.
Figure 14:
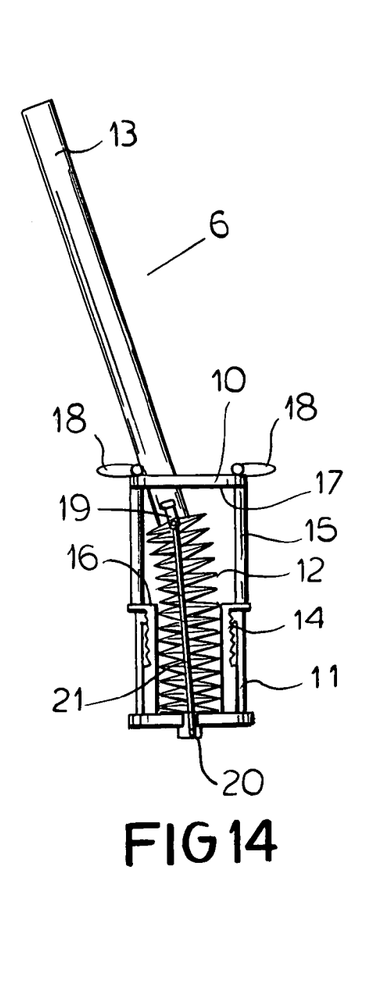
FIG. 14 shows a vertical section in the frontal plane of the lower part of a vertical rod disclosing the inclination sensor for the frontal plane, in which the upper part of the rod is inclined in the frontal plane.

The current angles of inclination of the vertical rods 6 are measured with two transducers which provide an output for the angle of inclination in the sagittal and the frontal plane, respectively. A transducer that has been developed for the purpose and is arranged for measuring the inclination in the frontal plane is shown in FIGS. 12–14 of which FIGS. 12 and 13 are sections in the sagittal plane and FIG. 14 shows a section in the frontal plane. The transducer comprises a slider 19 that is arranged in an opening in the stiff, upper part 13 of the vertical rod 6, the slider 19 being slidable in the longitudinal direction of the upper part 13 so as to compensate for the change in distance between the upper part 13 during change in angle of inclination, and a variable resistor 20, a trim potentiometer, mounted on the base cylinder 11 or the base plate 3. The slider 19 and the variable resistor 20 are connected with a thin-plate rod 21 which is wider in the frontal plane than in the sagittal plane so that the rod 21 will bend as a result of inclination in the sagittal plane, as shown in FIG. 13, whereas an inclination in the frontal plane will result in a rotation of the pin of the variable resistor 20 and thus a change of its resistance which may be provided as an output being indicative of the angle of inclination in the frontal plane. A similar transducer is provided at the other vertical rod 6 for measuring the angle of inclination in the sagittal plane.

Figure 15:
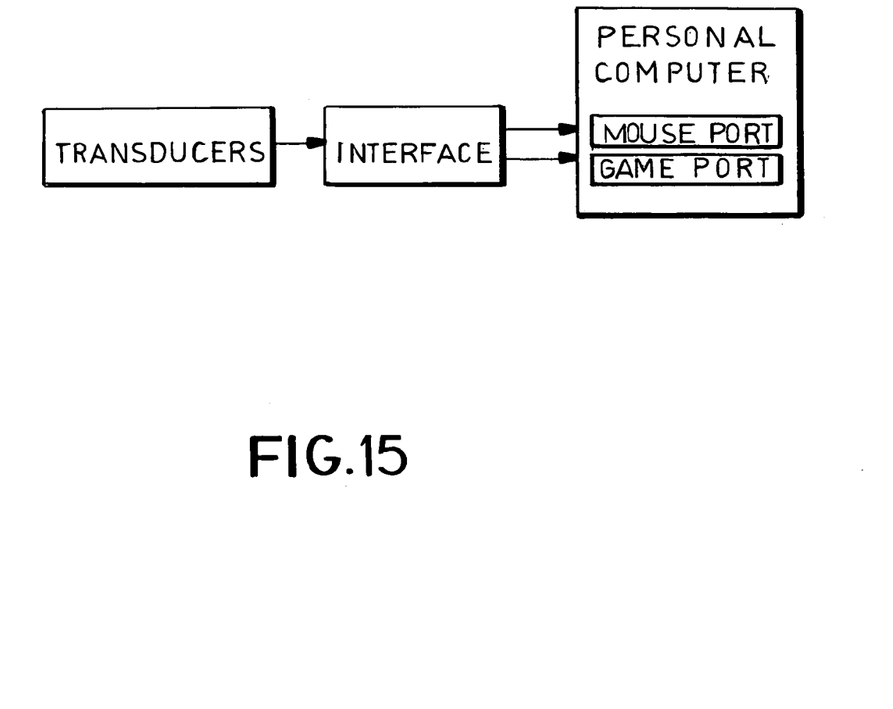
FIG. 15 is a schematic representation of the linking of the sensors and the personal computer, FIG. 16 are diagrams of the dead zone and the mouse velocities as function of the inclination in the frontal and sagittal planes for use with computer training, and FIG. 17 A–D shows four screen pictures of the computer training program.

The signals from the transducers are led to an electronic interface that transforms both angles of inclination of the apparatus into the computer mouse and/or joystick signals, connected to the mouse port and/or the game port of the personal computer, which is schematically represented in FIG. 15.

Figure 16:
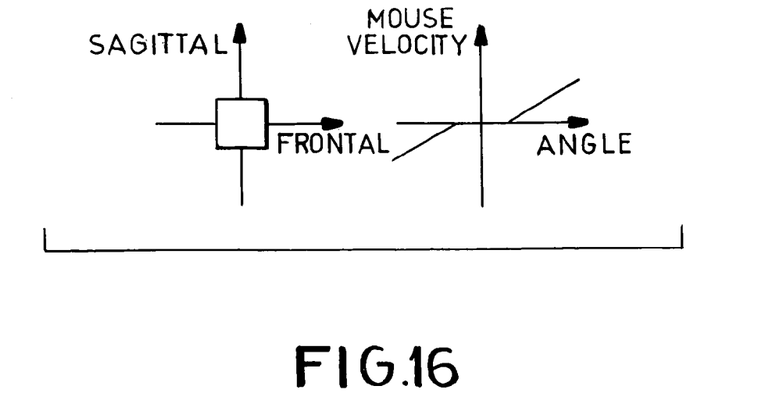

The function of the interface is depicted in two plots of FIG. 16. In the left plot the middle, square area denotes a dead zone in both inclination angles where no changes are signaled to the computer. This is equivalent to the output of the computer mouse, which does not undergo a change in position or to the state of the joystick when held in a neutral position. A person, standing in the apparatus, is faced with the screen of a PC as shown in FIG. 1. For moving the cursor on the screen in the desired direction the subject has to change posture in either the sagittal or frontal plane or in both planes simultaneously. If the dead zone is set to, for example ±5 degrees in both planes of motion, the subject will be performing ankle and hip movement in a range of at least ±5 degrees while trying to move the cursor on the screen or while trying to change the state of the joystick. On the right plot a possible relationship between the current angle of inclination in each plane and the speed of moving cursor on the computer screen is shown. As long as the dead zone is not exceeded the output from the interface does not change. The amount of angle exceeding the dead zone is manifested in a linear increase of the cursor speed, however other relationships can be implemented. The mouse buttons can be mounted to the bracing system within the reach of the standing subject.

By interfacing the apparatus with the PC we substitute the mouse and the joystick, which are predominant inputs in a majority of computer applications. In this way a standing subject exercises beneficial movement and balance training 1) through use of the advanced balance training and evaluation program software described below, 2) by playing his/her favorite computer game, and/or 3) by working with other computer applications. By doing that a standing subject perturbs and restores his equilibrium by which inherently re-trains the residual central and peripheral nervous system and develops alternative balance strategies.

With an adequate choice of supporting stiffness provided by the variable spring systems a 5 large portion of the population being affected by various disabilities, preventing them to stand without aid, would be able to re-train their balance abilities.

Advanced balance training and evaluation program.

Another advantageous component that may be used with the apparatus of the invention as well as with other similar training devices is an advanced balance training and evaluation computer program, which provide means 1) to set-up balance training program for individual person and 2) to objectively evaluate particular subject's balancing abilities. An objective evaluation is necessary to provide subjects and therapists with feedback on the improvement of their balancing abilities resulting from daily exercise in the apparatus. An example of computer software algorithm for balance training and evaluation of neurological impaired subjects while standing in the apparatus at given levels of support provided by the variable spring system and given dead zones implemented through electronic interface as described above is given below.

Figure 17:
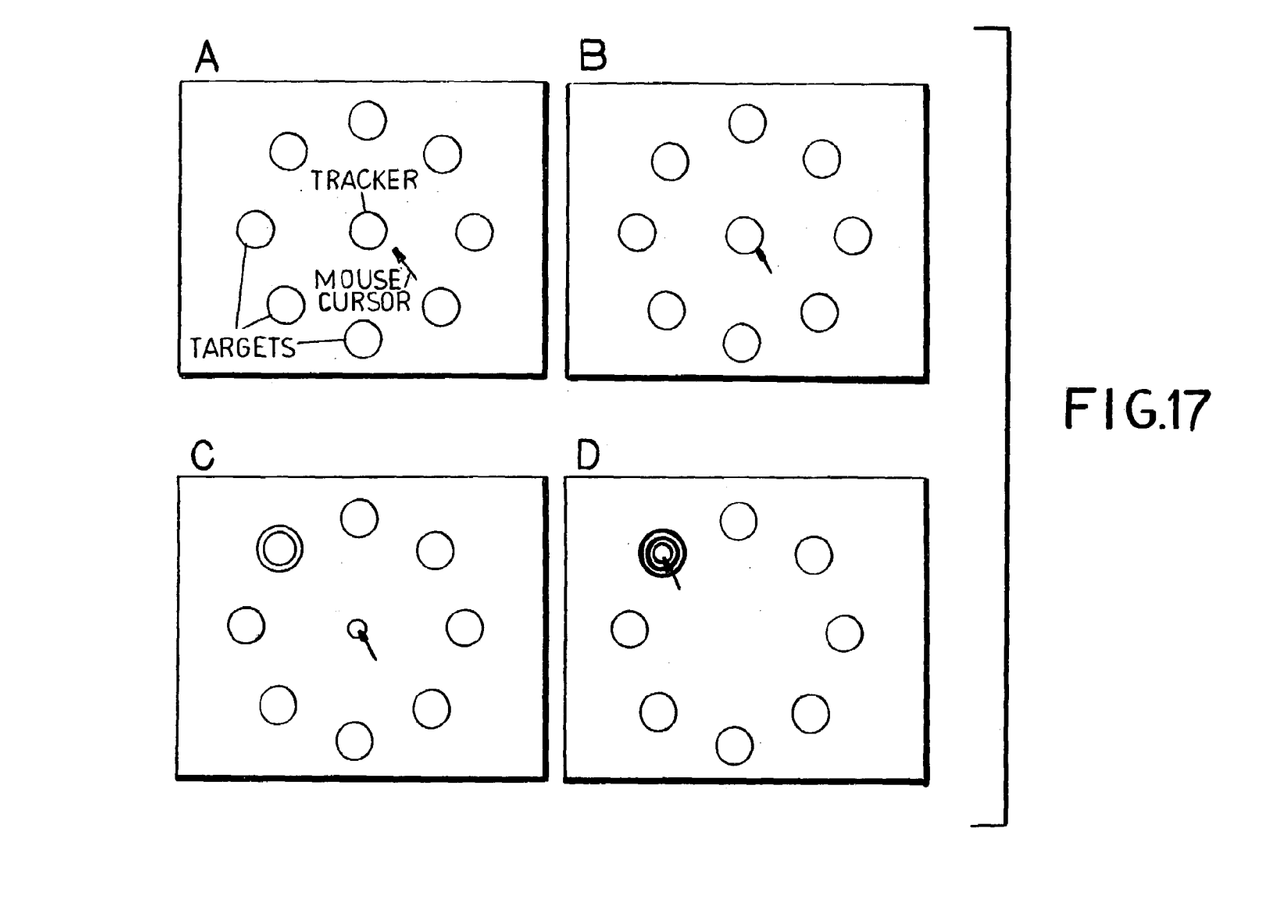

FIG. 17 A–D shows four screen pictures of the computer training program. The first scene appearing on the computer screen is shown in FIG. 17 A. In the middle of the computer screen an object, which in this case has a form of a circle (but could be of another shape), appears. We name this circle a tracker. Around the tracker eight additional circles are drawn in such a way to form a symmetrical object, which elements are equidistant to the tracker. Each circle from this symmetrical object is termed as a target. The number of targets can be different from eight, which we use in illustrative example. All the targets are of the same size (in case of circles the same diameter), while the tracker size (in case of a circle the diameter) can vary. For example it can be 10%, 30%, 50%, 70% and 90% of the targets size, thus, representing five different difficulty levels. The objective of the standing subject is to bring the tracker into one of the selected targets and keep it there for a period of time. This is termed as a tracking attempt.

The algorithm can be summarized in the following successive steps:

step 1 (FIG. 17 B): The first task for a standing subject is to move the mouse cursor into the area occupied by the tracker. The size of the tracker at this point is the same as the one of the targets. Once the mouse cursor is brought into that area a tracking attempt is initiated and the tracker becomes locked to the mouse cursor. i.e. thereafter, it moves as the mouse cursor moves.

step 2 (FIG. 17 C): When the tracker is locked to the mouse cursor, one of the targets, selected randomly, becomes active and starts to blink, e.g. changes color between the two pre-determined colors, depicted as to bold in FIG. 17 C). At the same time the size of the tracker is changed to the one pre-specified difficulty level before the initiation of the session.

step 3 (FIG. 17 D): The second task is then to move the tracker into the active target in such a way that the whole area of the tracker is held in the area occupied by the active target for at least one-second. The time given at the subject's disposal for completing tracking attempt can be varied. As an example, we define two time intervals of different duration and we term them as slow and fast, for example 5 and 10 seconds, respectively. If the task of placing the tracker into the target and holding it there for given period is done before the specified time interval elapses then the tracking attempt is considered as successfully completed and this is signaled to the subject, e.g. by a high frequency sound beep. If on the other hand time interval elapses and the subject was not successful, this is also signaled, e.g. by a low frequency sound beep. The described signaling could take any other appropriate form.

step 4 (FIG. 17 A): After either subject successfully completes the task or the selected time interval is elapsed tracking attempt is finished and the tracker is unlocked from the mouse cursor, re-sized to have the same diameter as target circles and positioned back to the center of the computer screen while the outcome of tracking attempt is stored in the computers memory.

step 5: The algorithm is idle and waits until the standing subject chooses to initiate another tracking attempt by undertaking step I again.

The above five steps are repeated for a given number of repetitions constituting a trial.

For example if each target (representing eight directions of movement) is repeated five times (in random order, which is unknown to the standing subject) then total of forty 35 tracking attempts are undertaken within each trial.

When the trial is completed the score percentage is calculated for each of the eight targets. The score percentage is then used to grade the performance of the subject. For example a mean score percentage value calculated from score percentages from all individuals targets could be presented to the subject. Additionally, a more complex evaluation of the trial results is presented on the screen of the PC in a suitable way. For example at each target location a bar composed of e.g. five elements if five repetitions were utilized in a trial for each target, could appear. According to the number of successfully completed tracking attempts a corresponding number of bar elements would be illuminated. Additionally, another bar showing the results of the most successful trial (judged according to e.g. the mean percentage score) at the same conditions (variable spring system, dead zone, difficulty level and time interval) performed by the same subject in previous training sessions would be displayed. This comparison would visually show the improvement or decline in subject's balancing performance. Another indication of improvement will be obvious from changed trial conditions (variable spring system, dead zone, difficulty level and time interval). The improvement will be shown by decreased support of variable spring system, increased dead zone (increased postural space), increased difficulty level (increased precision of fine regulation of desired posture) and decreased time interval (increased speed of postural response). The above description of scoring system is just an example. Other scorings of a trial could be utilized.

The key idea about the proposed algorithm for training and evaluation of balancing abilities is to provide an uniform neuro-rehabilitation program, which allows for direct comparison of balancing abilities of a particular subject between different trials as well as direct comparison between different trials performed by different subjects. The improvement in balancing abilities can be directly observed from decreased/increased parameters (variable spring system, dead zone, difficulty level and time interval).

It is clear from the above that the usage of the device is not confined only to neurologically impaired but is also suitable for balance training in sport, etc.

The invention claimed is:

1. A balance training apparatus comprising
   a base;
   two vertical supporting rods, each connected at a lower end to said base by a joint having two degrees of freedom;
   a brace for supporting the pelvis of a user standing between the two vertical supporting rods, the brace being connected to an upper end of each of the vertical supporting rods by a joint having one degree of freedom allowing mutual movement between the brace and the vertical rods in a plane of the two vertical rods,
   means for biasing comprising a lower elastic part on at least one of the vertical rods and connecting a semi-rigid upper part of one of said rods to said base for biasing the user towards an upright position when deviating therefrom in a frontal plane as well as in a sagittal plane of the user, said lower elastic part constituting the joint between the base and the lower end of said one of said rods; and
   an adjustment device for adjusting the stiffness of the lower elastic part.

2. An apparatus according to claim 1, wherein each of the two vertical rods has a respective said lower elastic part connecting said semi-rigid upper part of the respective rod to the base and connecting the joint therebetween as well as biasing the user toward the upright position.

3. An apparatus according to claim 2 wherein the elastic parts are connected to respective vertical helical springs.

4. An apparatus according to claim 3 further comprising respective limitators for limiting the angle of inclination from vertical for each of the vertical rods.

5. An apparatus according to claim 4 wherein the adjustment device configured to adjust the stiffness of the lower elastic part by adjusting an effective length thereof.

6. An apparatus according to claim 5 wherein the adjustment for each said vertical spporting rod comprises an outer sleeve arranged around the elastic part with an inner, vertical surface of the sleeve fitting around the outer side of the elastic part, the sleeve being vertically displaceable such that the effective length of the elastic part is adjusted thereby.

7. An apparatus according to claim 6, wherein limitators define circular openings through which the vertical rods pass, and wherein the limitators are connected to the and are displaced together therewith.

8. An apparatus according to claim 1, further comprising locking means for temporarily locking each of the vertical rods in a vertical position.

9. An apparatus according to claim 8 wherein the locking means are connected to the sleeves and are displaced together therewith.

10. An apparatus according to claim 1, further comprising knee supports arranged to support the front side of both legs of the user near an upper end of the shanks, the knee supports being arranged to follow the movements of the user in the frontal plane as well as in the sagittal plane.

11. An apparatus according to claim 10 wherein the knee supports are compliant.

12. An apparatus according to claim 11 wherein the compliance of the knee supports is adjustable.

13. An apparatus according to claim 1, further comprising sensors for measuring the inclination of in the frontal plane as well as in the sagittal plane of the vertical rods and producing an output.

14. A balance training apparatus comprising two vertical supportive rods, each connected at a lower end to a base by a joint having two degrees of freedom, a brace for supporting the pelvis of a user standing between the two vertical supporting rods, the brace being connected to an upper end of each of the vertical supportive rods by a joint having one degree of freedom allowing mutual movement between the brace and the vertical rods in a plane of the two vertical rods, biasing means for biasing the user towards an upright position when deviating therefrom in a frontal plane as well as in a sagittal plane of the user, and compliant knee supports arranged to support the front side of both legs of the user near an upper end of the shanks, the knee supporting means being arranged to follow the movements of the user in the frontal plane as well as in the sagittal plane.

15. An apparatus according to claim 14 wherein the compliance of the knee supports is adjustable.

16. An apparatus according to claim 14 wherein the knee supports are connected to at least one of the vertical rods.

* * * * *